(12) United States Patent
Tuan et al.

(10) Patent No.: US 10,802,298 B2
(45) Date of Patent: Oct. 13, 2020

(54) EYE MOUNTED DEVICE FOR CONTROLLING FOCUSING DISORDERS

(71) Applicant: Spy Eye, LLC, Los Gatos, CA (US)

(72) Inventors: Kuang-mon Ashley Tuan, Mountain View, CA (US); Michael Frank Deering, Los Altos, CA (US)

(73) Assignee: Tectus Corporation, Saratoga, CA (US)

( * ) Notice: Subject to any disclaimer, the term of this patent is extended or adjusted under 35 U.S.C. 154(b) by 311 days.

(21) Appl. No.: 15/639,514

(22) Filed: Jun. 30, 2017

(65) Prior Publication Data

US 2018/0017814 A1    Jan. 18, 2018

Related U.S. Application Data

(60) Provisional application No. 62/363,127, filed on Jul. 15, 2016.

(51) Int. Cl.
| | | |
|---|---|---|
| *G02C 11/00* | (2006.01) | |
| *G02C 7/04* | (2006.01) | |
| *G03B 21/14* | (2006.01) | |
| *A61B 3/107* | (2006.01) | |
| *A61B 3/00* | (2006.01) | |
| *A61H 5/00* | (2006.01) | |

(52) U.S. Cl.
CPC ............ *G02C 11/10* (2013.01); *A61B 3/0008* (2013.01); *A61B 3/107* (2013.01); *A61H 5/00* (2013.01); *A61H 5/005* (2013.01); *G02C 7/04* (2013.01); *G03B 21/145* (2013.01); *G02C 2202/24* (2013.01)

(58) Field of Classification Search
CPC ...... G02C 11/10; G02C 7/04; G02C 2202/24; A61B 3/0008; A61B 3/107; A61B 5/00; A61B 5/005; A61H 5/00; A61H 5/005; G03B 21/145
See application file for complete search history.

(56) References Cited

U.S. PATENT DOCUMENTS

| | | | |
|---|---|---|---|
| 6,752,499 | B2 | 6/2004 | Aller |
| 7,637,612 | B2 | 12/2009 | Menezes |
| 7,832,859 | B2 | 11/2010 | Philips |
| 8,485,662 | B2 | 7/2013 | Collins et al. |
| 8,672,473 | B2 | 3/2014 | Martinez et al. |
| 8,786,675 | B2 | 7/2014 | Deering |
| 8,899,746 | B2 | 12/2014 | Back |
| 9,074,750 | B2 | 7/2015 | Foulds et al. |
| 9,804,416 | B2 * | 10/2017 | Pugh ..................... G02C 7/046 |
| 9,837,052 | B2 * | 12/2017 | Deering ............ G02B 27/0172 |

(Continued)

OTHER PUBLICATIONS

Aldossari, H. et al., "Effect of Accommodation on Peripheral Eye Lengths of Emmetropes and Myopes," Optometry and Vision Science, 2016, pp. 361-369, vol. 94, No. 3.

(Continued)

*Primary Examiner* — Collin X Beatty

(74) *Attorney, Agent, or Firm* — Fenwick & West LLP

(57) ABSTRACT

An eye mounted display presents defocused images to patients to affect their eyeball development and control focusing disorders such as myopia or hyperopia. For example, images may be projected with peripheral myopic defocus in order to control myopia. Images may be projected with peripheral hyperopic defocus in order to control hyperopia.

11 Claims, 6 Drawing Sheets

(56) References Cited

U.S. PATENT DOCUMENTS

| | | | |
|---|---|---|---|
| 2004/0237971 A1* | 12/2004 | Radhakrishnan | A61B 3/103 |
| | | | 128/898 |
| 2009/0189974 A1* | 7/2009 | Deering | G09G 3/02 |
| | | | 348/46 |
| 2011/0051079 A1* | 3/2011 | Martinez | G02C 7/02 |
| | | | 351/159.34 |
| 2014/0081357 A1 | 3/2014 | Legerton et al. | |
| 2014/0268035 A1* | 9/2014 | Pugh | G02C 7/04 |
| | | | 351/159.81 |
| 2015/0234206 A1* | 8/2015 | Lee | G02C 7/085 |
| | | | 351/206 |
| 2015/0312560 A1 | 10/2015 | Deering et al. | |
| 2017/0276963 A1* | 9/2017 | Brennan | G02B 27/0075 |

OTHER PUBLICATIONS

Allinjawi, K. et al., "Peripheral Refraction with Different Designs of Progressive Soft Contact Lenses in Myopes," F1000Research, 2016, pp. 1-11, vol. 5, No. 2742.

Anstice, N. et al., "Effect of Dual-Focus Soft Contact Lens Wear on Axial Myopia Progression in Children," Ophthalmology, 2011, pp. 1152-1161, vol. 6.

Dolgin, E., "The Myopia Boom," Nature, Mar. 19, 2015, pp. 276-278, vol. 519.

Jones, L. et al., "Parental History of Myopia, Sports and Outdoor Activities, and Future Myopia, Investigative Ophthalmology and Visual Science," Invest. Opthalmol. Vis. Sci., Aug. 2007, pp. 3524-3532, vol. 48, No. 8.

Lan, W. et al., Intermittent Episodes of Bright Light Suppress Myopia in the Chicken More than Continuous Bright Light, PLOS One, vol. 9, p. e110906, (2014).

Ossola, A., "The Surprising Amount of Time Kids Spend Looking at Screens," the Atlantic, Jan 22, 2015, 5 pages.

Rohrer, B. et al., "Stimulation of Dopaminergic Amacrine Cells by Stroboscopic Illumination or Fibroblast Growth Factor (bFGF, FGF-2) Injections: Possible Roles in Prevention of Form-Deprivation Myopia in the Chick," Brain Research, 1995, pp. 169-181, vol. 686.

Rose, K. A. et al., "Myopia, Lifestyle, and Schooling in Students of Chinese Ethnicity in Singapore and Sydney," Archives of Ophthalmology, Apr. 2008, pp. 527-530, vol. 126.

Rucker, F. et al., "Blue Light Protects Against Temporal Frequency Sensitive Refractive Changes," Investigative Ophthalmology and Visual Science, 2015, pp. 6121-6131, vol. 56.

Thorn, F. et al., "Myopia Progression Is Specified by a Double Exponential Growth Function," Optometry and Vision Science, Apr. 2005, p. E286, 12 pages, vol. 82, No. 4.

Wang, Y. et al., "Exposure to Sunlight Reduces the Risk of Myopia in Rhesus Monkeys," PLOS One, Jun. 1, 2015, p. e0127863, 16 pages, vol. 10.

Wu, P.-C. et al., "Outdoor Activity during Class Recess Reduces Myopia Onset and Progression in School Children," Ophthalmology, 2013, pp. 1080-1085, vol. 5.

* cited by examiner

| Problem | Treatment | Description |
|---|---|---|
| Myopia | Myopic defocus | peripheral images focused inside eyeball, before retina |
| Hyperopia | Hyperopic defocus | peripheral images focused outside eyeball, after retina |
| Accommodative lag | Central myopic defocus | central images focused on retina and before retina |
| Myopia | Enhance blue | project images with extra brightness in the blue part of the spectrum |

Fig. 5

EYE MOUNTED DEVICE FOR CONTROLLING FOCUSING DISORDERS

CROSS-REFERENCE TO RELATED APPLICATIONS

This application claims priority under 35 U.S.C. § 119(e) to U.S. Provisional Patent Applications Ser. No. 62/363,127, "Methods to attenuate eye growth," filed Jul. 15, 2016. The subject matter of all of the foregoing is incorporated herein by reference in its entirety.

BACKGROUND

Myopia, or nearsightedness, is a widespread problem. Myopia increases the risk of other vision problems including cataracts and glaucoma, yet it is still not clear what causes myopia or how to control it. Although myopia is partly hereditary, aspects of childhood lifestyle such as time spent in near work reading books or staring at screens versus time spent outside seem to be predictive.

Treatments for myopia have evolved over the years. Exposure to bright light, blue light, or playing outdoors have been suggested as preventative measures for children with developing myopia or whose eyes have an inability to accurately accommodate.

Other approaches take note of animal studies suggesting that accommodative lag triggers an increase in eye growth which causes myopia. See e.g. U.S. Pat. No. 6,752,499 by Aller. "Hyperopic defocus" means that images which should be focused on the retina by the cornea and the eye's crystalline lens are instead focused beyond the retina. This condition can be caused by an eye's inability to accommodate, or change focus sufficiently, when viewing objects at different distances. For example, when looking at close objects, the eye may not fully accommodate leading to hyperopic defocus. As another example, if the eyeball is elongated (i.e. oblong or not spherical), then an image that falls on a perfect sphere may be in-focus at the center but exhibit hyperopic defocus in the periphery. It appears that a developing eyeball grows so as to bring images into focus. In the presence of hyperopic defocus, the eyeball grows proportionally longer to meet the image, thus causing or exacerbating myopia.

Similarly in the presence of myopic defocus—images formed before the retina rather than on it—the eyeball grows proportionally shorter to meet the image. Several researchers have therefore proposed, and conducted studies to test, the idea of presenting images that are focused before the retina to children with developing myopia. Such intentional myopic defocus may be achieved with multifocal contact lenses. The lenses may be made with annular zones or rings having different focal properties. See e.g. U.S. Pat. No. 7,832,859. A central portion of the lens focuses images on the retina taking into account whatever refractive correction a particular subject may need. Concentric rings around the central portion focus images with a few diopters' myopic defocus. A child wearing the lens experiences two images simultaneously: one that corrects their vision and one that is blurry because it is focused before their retina. Anstice et al. have published clinical study evidence suggesting that dual-focus contact lenses can slow down the development of myopia (*Effect of Dual-Focus Soft Contact Lens Wear on Axial Myopia Progression in Children*, Ophthalmology, volume 6, pages 1152-1161 (2011)).

At the same time that humanity is becoming ever more nearsighted, our consumption of digital media by staring at video displays is skyrocketing. Estimates of average screen time ranging from six to ten hours per day are common. New kinds of displays are being developed to satisfy the apparently insatiable demand for video entertainment. Head-mounted displays, such as augmented reality headsets and smart glasses are becoming popular. Prolonged use of these devices may indirectly promote progression of myopia.

Thus, there is a need for systems and methods to control myopia and other focusing disorders in an age when increased consumption of digital media is rampant.

FIGURES

FIG. 5 is a table of eye conditions and treatments for children.

DESCRIPTION

Figure 1:
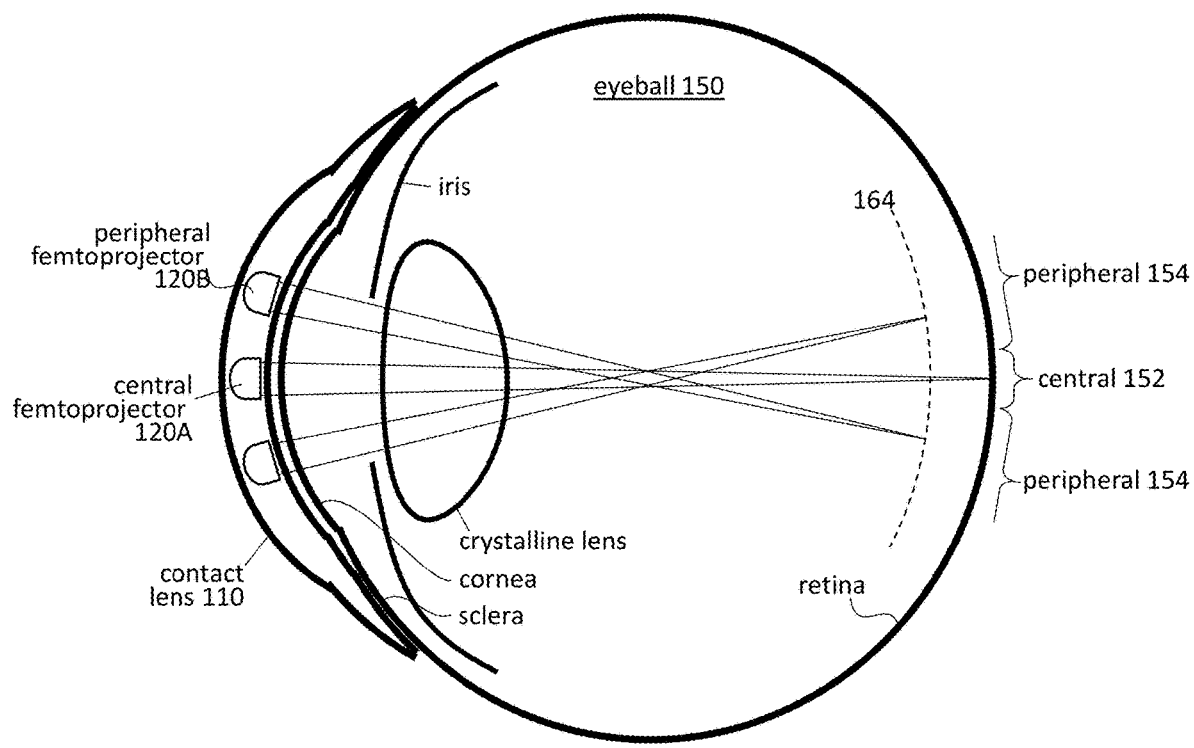
FIG. 1 is a cross-sectional diagram of a femtoprojector array mounted in a contact lens as worn on a person's eyeball.

One category of displays is called an eye-mounted display. See, e.g. U.S. Pat. No. 8,786,675, "Systems using eye mounted displays". One type of eye-mounted display is based on tiny projectors, each one no larger than about a millimeter in any dimension, mounted inside a contact lens. Deering called these devices "femtoprojectors". They project images onto the retina of a person wearing the contact lens.

A femtoprojector includes an image source and an optical system. The image source may be a display chip that includes an array of light-emitting pixels. A light emitting diode (LED) array is an example of a display chip. The optical system includes lenses and/or mirrors that focus light from the image source onto the retina. A femtoprojector may be aimed at a specific part of the retina.

Myopia control with defocused femtoprojectors is an example of the use of an eye-mounted display to affect eyeball growth and thereby contain the development of eye focusing disorders in children. Femtoprojectors in a contact lens may project images that are focused before, on, or after the retina. Furthermore, femtoprojectors may project images with certain parts of the visual spectrum enhanced as compared to a normal image.

Eye-mounted displays such as contact lens displays or displays mounted in intraocular lenses differ from all other displays in that they are fixed to the eye; i.e. they move with the eyeball. Unlike TV screens, mobile devices, newspapers, etc., eye-mounted displays present images that cannot be perused or surveyed. The content of a scene—the pictures or words that are shown—may be altered by sending different data to the display, but absent changes in content, one cannot move his or her eye to view a different part of an image.

The spatial resolution of an eye-mounted display may be matched to the spatial resolution of the retina. Eye-mounted displays require less data per video frame than conventional displays because high resolution is only necessary near the fovea of the retina. Away from the fovea, in the periphery, the retina has relatively poor spatial resolution so it is less useful to render pixels there at high resolution. Our sensation of being able to see well in all directions is a consequence of being able to move our eyeballs rapidly, not great peripheral vision.

A contact lens display may be based on an array of femtoprojectors mounted in the contact lens. Each femtoprojector may be aimed at a specific area on the retina. Femtoprojectors aimed at low resolution parts of the retina may project lower resolution pixels than those aimed at the fovea. Furthermore, femtoprojectors aimed at different parts of the retina may be focused differently. Some femtoprojectors may be set to produce images focused on the retina while others may be set to have myopic or hyperopic defocus.

In addition, femtoprojectors may project images that over- or underemphasize certain parts of the visual spectrum. Humans can see light ranging from about 400 nm to about 700 nm in wavelength. Roughly speaking, wavelengths in the band from 620 to 700 nm are perceived as red, those in the band from 495 nm to 570 nm are perceived as green, and those in the band from 450 nm to 495 nm are perceived as blue. A femtoprojector may show an image in which blue wavelengths are displayed more brightly than normal, as an example. Alternatively a white background may appear more blue than normal.

Eye-mounted displays are discreet. They may be unnoticeable to people other than the wearer. Since modern children watch screens interminably and are likely to watch even longer in the future, it makes sense to treat their eye disorders while they are absorbed in digital worlds. Hence, myopia control with defocused femtoprojectors encompasses systems and methods to present video to children with specially defocused images in an effort to modify their natural eyeball growth.

Turning now to the drawings, FIG. 1 is a cross-sectional diagram of a femtoprojector array 120 mounted in a contact lens 110 as worn on a person's eyeball 150. The femtoprojector array 120 has peripheral myopic defocus. The eyeball is ordinary in all respects; some parts are called out for clarity: retina, sclera, cornea, iris, crystalline lens. The part of the retina near the fovea, the center of the visual field, is marked "central 152" while areas of the fovea away from the fovea are marked "peripheral 154". The central area 152 of the retina may be any part within about five to about ten degrees of the visual axis. The peripheral area 154 of the retina may include any other part of the retina that is not in the central area.

Mounted on the eyeball is a scleral contact lens 110. In other approaches, other types of contact lens could be used, such as soft lenses and hybrid lenses. The contact lens contains an array of femtoprojectors 120, such as those described in U.S. Pat. No. 8,786,675, "Systems using eye mounted displays" or US 2015/0312560, "Variable resolution eye mounted displays", both of which are incorporated herein by reference. The central femtoprojector 120A is aimed at the central area 152 of the retina. One or more peripheral femtoprojectors 120B are aimed at peripheral areas 154 of the retina.

The central femtoprojector 120A is focused on the retina. It triggers the eyeball's accommodation response. A peripheral femtoprojector 120B is focused before the retina, inside the eyeball. The dashed line 164 in the figure shows the focal surface of the peripheral femtoprojector 120B. Although the dashed line in the figure gives the impression that the amount of the peripheral femtoprojector's myopic defocus might be as much as 5% of the length of the eyeball, it may be much less in practice. A +2 diopter defocus in a 20 mm eyeball with 50 diopters natural focusing power moves the focal surface about 400 microns in front of the retina, for example. The defocus preferably is less than three diopters.

Figure 2:
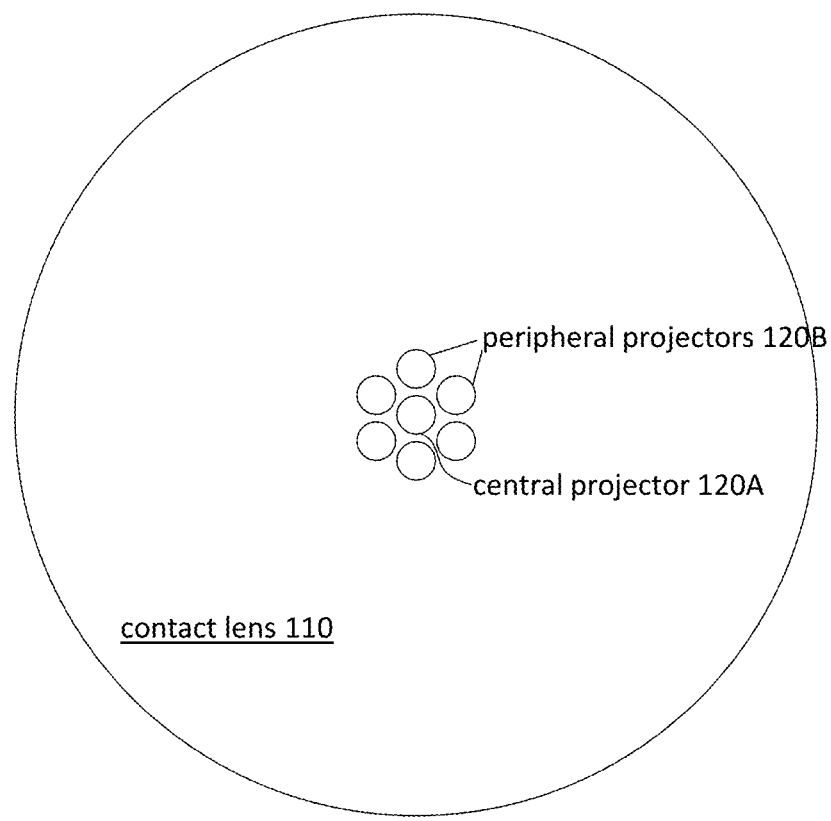
FIG. 2 is a top view of a femtoprojector array mounted in a contact lens.

FIG. 2 is a top view of a femtoprojector array mounted in a contact lens 110. There are one central projector 120A and six peripheral projectors 120B shown in the figure. However, an eye-mounted display realized with femtoprojectors in a contact lens may have a group of more than one central projector and a group with some number of peripheral projectors other than six. Furthermore, the central projector (s) need not be located in the center of the array of femtoprojectors installed in a contact lens. What makes a central projector "central" is the area of the retina at which the projector is aimed, not the location of the projector in the contact lens. Nevertheless the arrangement shown in FIG. 2 is typical, albeit not required. Comparing FIGS. 1 and 2, it is apparent that while only one central and two peripheral femtoprojectors are illustrated in FIG. 1, other femtoprojectors could be included.

Figure 3:
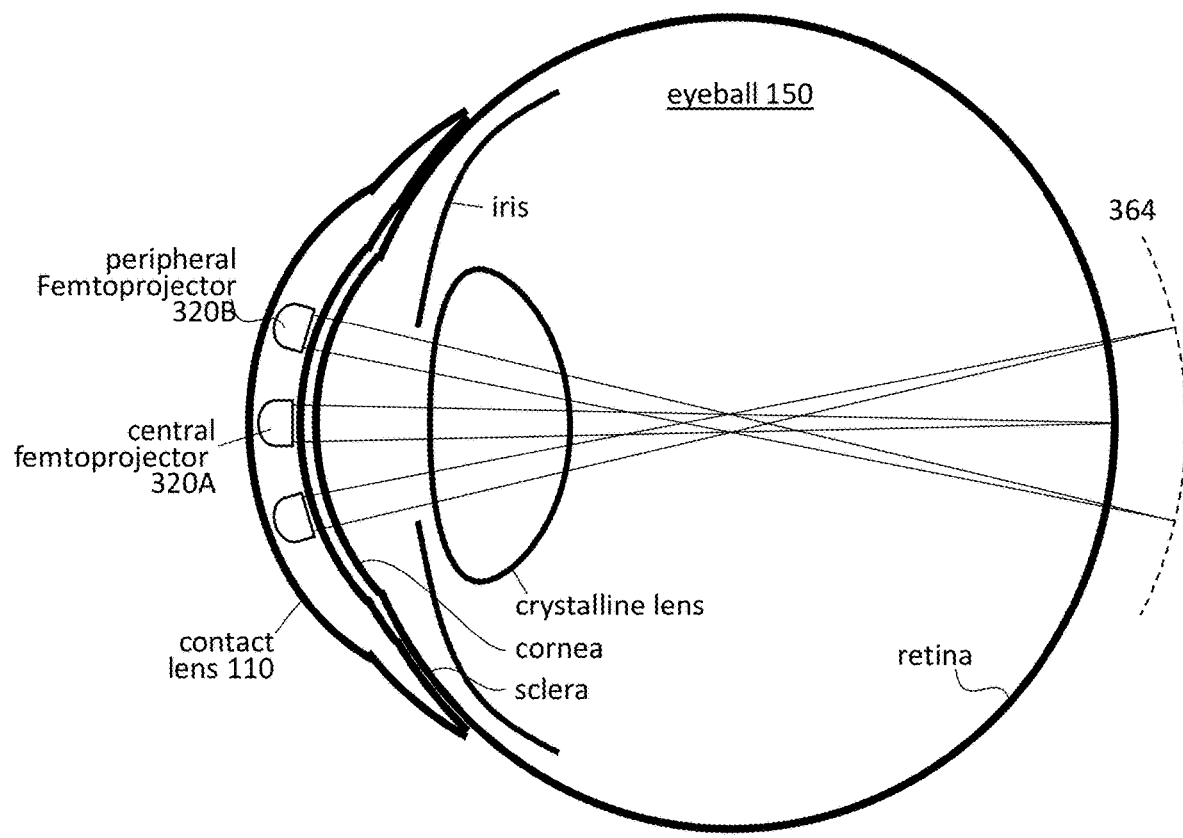
FIG. 3 is a cross-sectional diagram of a femtoprojector array mounted in a contact lens as worn on a person's eyeball.

FIG. 3 is a cross-sectional diagram of a femtoprojector array mounted in a contact lens 110 as worn on a person's eyeball 150. FIG. 3 is similar to FIG. 1 except that in FIG. 3 peripheral femtoprojectors 320B are illustrated with hyperopic defocus—they focus on the dashed line 364 beyond the retina rather than in front of it. The "central" and "peripheral" labels of FIG. 1 and associated description apply to FIG. 3 as well; they are omitted only for clarity to keep the drawing from becoming cluttered.

Although the dashed line 364 in the figure gives the impression that the amount of the peripheral femtoprojector's hyperopic defocus might be as much as 5% of the length of the eyeball, it may be much less in practice. A −2 diopter defocus in a 20 mm eyeball with 50 diopters natural focusing power moves the focal surface about 400 microns behind the retina, for example. The defocus preferably is less than three diopters.

Figure 4:
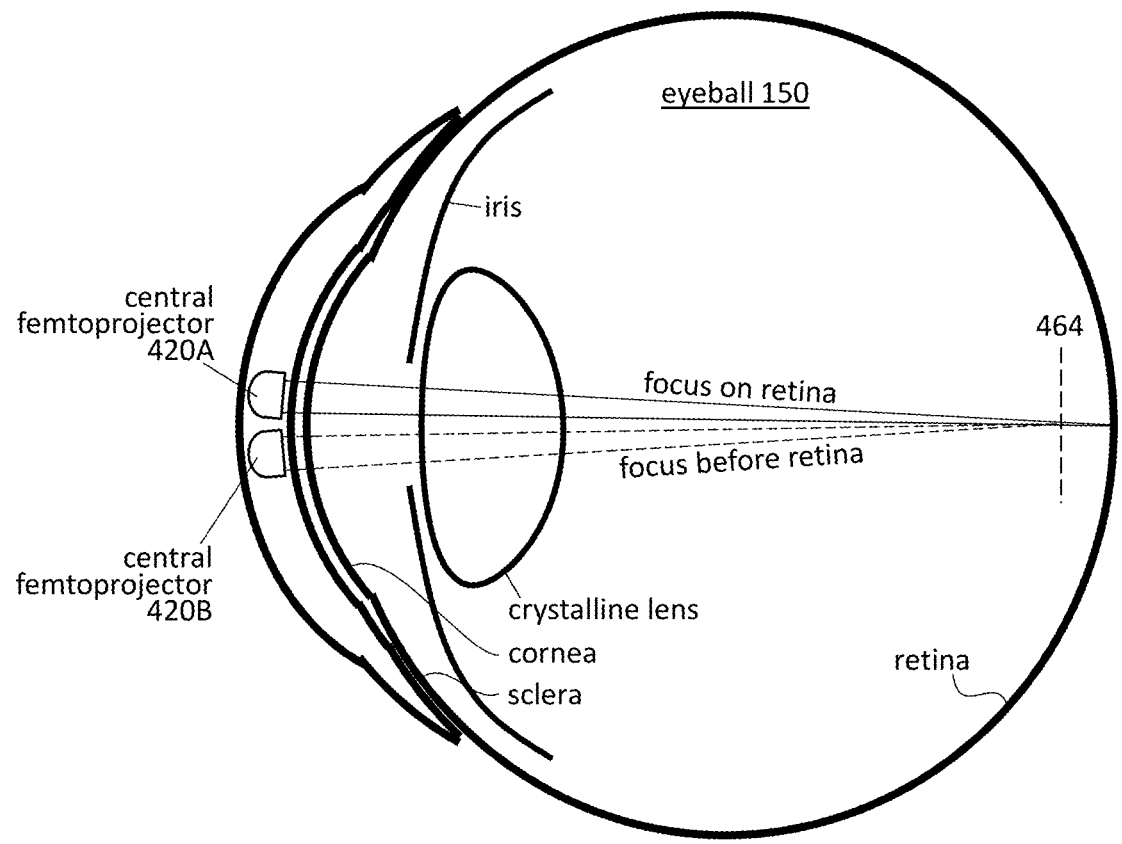
FIG. 4 is a cross-sectional diagram of a femtoprojector array mounted in a contact lens as worn on a person's eyeball.

FIG. 4 is a cross-sectional diagram of a femtoprojector array mounted in a contact lens 110 as worn on a person's eyeball 150. FIG. 4 is similar to FIGS. 1 and 3 except that the configuration of femtoprojectors is different. The system of FIG. 4 includes two central projectors: one 420A is focused on the retina, and the other 420B is focused before the retina at the dashed line 464. The femtoprojector 420B projects images with central myopic defocus. All of the central projectors are aimed in the central field of view; i.e. at the fovea and its surroundings. In fact, the central projectors 420 may all be aimed at exactly the same area of the retina. A person wearing the contact lens illustrated in FIG. 4 sees an image in focus on his or her retina and also the same image presented with myopic defocus. As discussed above, the amount of myopic defocus in an actual system is less than that shown in the figure.

The capability of a femtoprojector array in a contact lens to simultaneously present focused images at the fovea and intentionally defocused images in the periphery (or at the fovea) lends itself to treating focusing disorders such as myopia, hyperopia and accommodative lag in children. Myopia and hyperopia may be treated by presenting slightly out-of-focus images. Long exposure to such images, even if they are only seen in the periphery of the retina, may affect the development of a child's eyeball such that myopia or hyperopia is reduced. Accommodative lag (a failure of the eye to accommodate properly) may be treated by presenting slightly out-of-focus images in the center of the retina at the same time as properly focused images.

FIG. 5 is a table of eye conditions and treatments, especially for children and those under 18 years of age or whose eyes are still growing. For example, children with myopia may be helped by seeing images with peripheral myopic defocus while their central vision is corrected conventionally. Such images may be obtained with a contact lens system like that shown in FIG. 1. The contact lens may be designed to provide sphere and cylinder correction as needed for conventional vision correction. In addition, images are presented by a femtoprojector array such that they are in focus at or near the fovea, but myopically defocused in the periphery.

Children with hyperopia may be helped by seeing images with peripheral hyperopic defocus while their central vision is corrected conventionally. Such images may be obtained with a contact lens system like that shown in FIG. 3. The contact lens may be designed to provide sphere and cylinder correction as needed for conventional vision correction. In addition, images are presented by a femtoprojector array such that they are in focus at or near the fovea, but hyperopically defocused in the periphery.

Accommodative lag may be addressed by displaying images that are simultaneously in focus at the retina in central vision and also myopically defocused in the same part of the retina. This may be achieved with a contact lens system like that shown in FIG. 4. The contact lens may be designed to provide conventional sphere and cylinder correction at the same time.

Femtoprojector arrays such as those shown in FIGS. 1-4 may, in addition to their specialized focusing properties, display images with unnatural color balance, especially in peripheral areas. Emphasizing the blue part of the visible spectrum is thought to reduce myopia during eyeball development.

Figure 6:
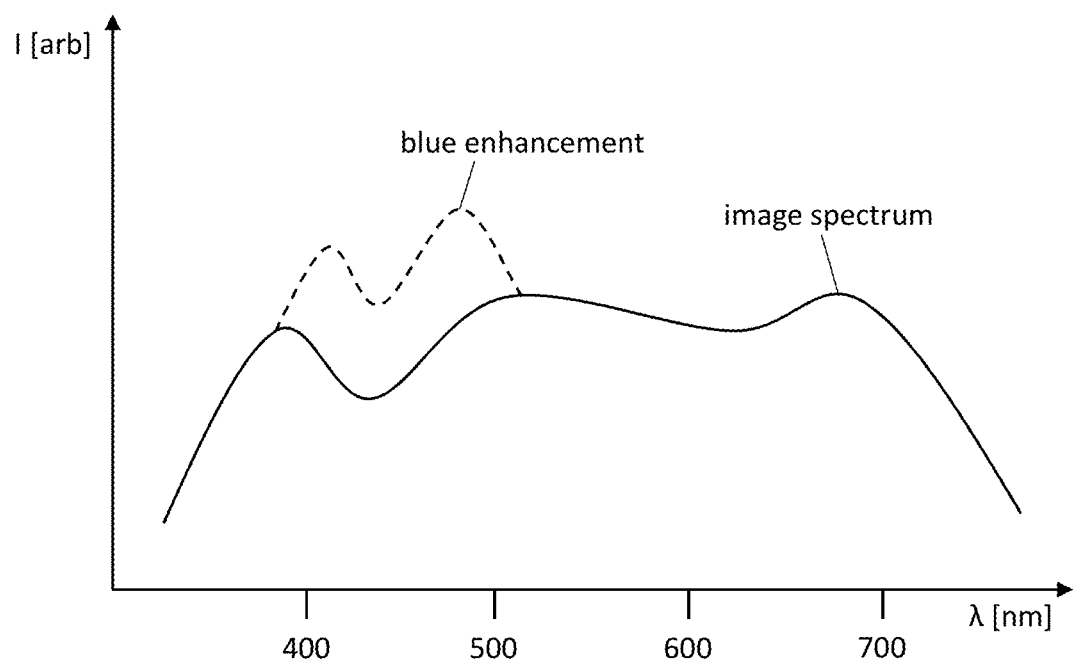
FIG. 6 is a graph of a visual spectrum pointing out blue enhancement.

FIG. 6 is a graph of a visual spectrum pointing out blue enhancement. In FIG. 6, an image spectrum is plotted on a graph of image intensity (in arbitrary units) versus wavelength (in nanometers). The image spectrum shows how bright different colors are in a certain image (not shown). A dashed line marked "blue enhancement" shows how the violet and blue part of an image—the wavelengths between about 400 nm and about 500 nm—may be increased in intensity. The best wavelength range for myopia control may be determined experimentally.

Eye-mounted displays, especially contact lens displays having an array of femtoprojectors, may be constructed to project images that affect children's eyeball development. Although effects on eyeball growth caused by defocused images take time to appear, children are becoming more and more immersed in digital content. Contact lens based displays can be used to present this digital content, such as augmented reality or virtual reality. In addition, they are continuously aligned with the retina so they can be used to present defocused images in particular parts of the retina for the purpose of controlling eye development. They can also be manufactured with different amounts of defocus and/or different focus positions for different projectors. The correct contact lens device can then be selected, for example to accommodate progression of the patient's eye or customized to the measured shape of the patient's eye. As another alternative, similar approaches may be used with eye mounted devices that project defocused light into the wearer's eye, but without necessarily projecting images or otherwise serving as a display device.

Although the detailed description contains many specifics, these should not be construed as limiting the scope of the invention but merely as illustrating different examples. It should be appreciated that the scope of the disclosure includes other embodiments not discussed in detail above. Various other modifications, changes and variations which will be apparent to those skilled in the art may be made in the arrangement, operation and details of the method and apparatus disclosed herein without departing from the spirit and scope as defined in the appended claims. Therefore, the scope of the invention should be determined by the appended claims and their legal equivalents.

What is claimed is:

1. A method of controlling eye focusing disorders in a patient, the method comprising:
   diagnosing an eye focusing disorder for the patient; and
   having the patient wear an eye mounted treatment device comprising:
      a contact lens; and
      a first group of one or more femtoprojectors mounted in the contact lens, the first group projecting light into the patient's eye, wherein said light is defocused to form images in front of or behind the patient's retina, and the defocus is selected based on stimulating eye growth to control the diagnosed eye focusing disorder.

2. The method of claim 1 where the patient is less than 18 years of age.

3. The method of claim 1 where the diagnosed eye focusing disorder is myopia and the first group projects light into the patient's eye with peripheral myopic defocus to form images in front of a peripheral area of the patient's retina.

4. The method of claim 1 where the diagnosed eye focusing disorder is hyperopia and the first group projects light into the patient's eye with peripheral hyperopic defocus to form images behind a peripheral area of the patient's retina.

5. The method of claim 1 where the diagnosed eye focusing disorder is accommodative lag and the first group projects light into the patient's eye with central myopic defocus to form images in front of a central area of the patient's retina.

6. The method of claim 1 further comprising:
   measuring a shape of the patient's eye; and
   selecting from a plurality of eye mounted treatment devices with different focus positions for the first group, based on the focus position of the first group relative to the shape of the patient's eye.

7. The method of claim 1 wherein the eye mounted treatment device further comprises a second group of one or more femtoprojectors mounted in the contact lens, the second group projecting light into the patient's eye, said light focused on the patient's retina.

8. The method of claim 2 wherein the second group projects light to a center area of the patient's retina, and the first group projects light to a peripheral area of the patient's retina.

9. The method of claim 2 wherein both the first and second group project light to a center area of the patient's retina.

10. The method of claim 1 wherein the first group also projects light with enhanced brightness in a blue region of a visible spectrum.

11. The method of claim 1 wherein the first group projects light into the patient's eye with defocus of not more than three diopters.

* * * * *